United States Patent [19]

Cornillault

[11] 4,274,741

[45] Jun. 23, 1981

[54] DEVICE FOR DETERMINING THE GRANULOMETRIC COMPOSITION OF A MIXTURE OF PARTICLES BY DIFFRACTION OF LIGHT

[75] Inventor: Jean Cornillault, Nozay, France

[73] Assignee: Compagnie Industrielle des Lasers, Marcoussis, France

[21] Appl. No.: 79,007

[22] Filed: Sep. 26, 1979

[51] Int. Cl.³ ............................................. G01N 15/02
[52] U.S. Cl. .................................... 356/336; 356/343; 250/574
[58] Field of Search ................ 356/336, 343; 250/564, 250/574; 350/162 SF

[56] References Cited

U.S. PATENT DOCUMENTS

| | | | |
|---|---|---|---|
| 3,310,680 | 3/1967 | Hasegawa | 356/343 |
| 3,705,771 | 12/1972 | Friedman et al. | 356/343 |
| 3,807,864 | 4/1974 | Cornillault | 356/336 |
| 4,070,113 | 1/1978 | Frazer et al. | 356/343 |
| 4,139,303 | 2/1979 | Carlson et al. | 356/336 |

FOREIGN PATENT DOCUMENTS 2340252  2/1974  Fed. Rep. of Germany ........... 356/343

Primary Examiner—Conrad J. Clark
Attorney, Agent, or Firm—Sughrue, Rothwell, Mion, Zinn and Macpeak

[57] ABSTRACT

The invention relates to a device for determining the granulometric composition of a mixture of particles by diffraction of light. The light flux received on the diffraction pattern is measured in a number of diffraction areas (AI,AJ) each of which is in the shape of an angular sector of circular rings which are concentric with the pattern, these integration areas forming two successions in each of which the inner and outer radii form geometrical progressions with common ratio of two, the ratio between the outer radius and the inner radius of an integration area being chosen in the interval between two and the square root of two, the radii within one succession (AJ) being equal to those within the other (AI) multiplied by the square root of two. Application to studying powder mixtures.

9 Claims, 5 Drawing Figures

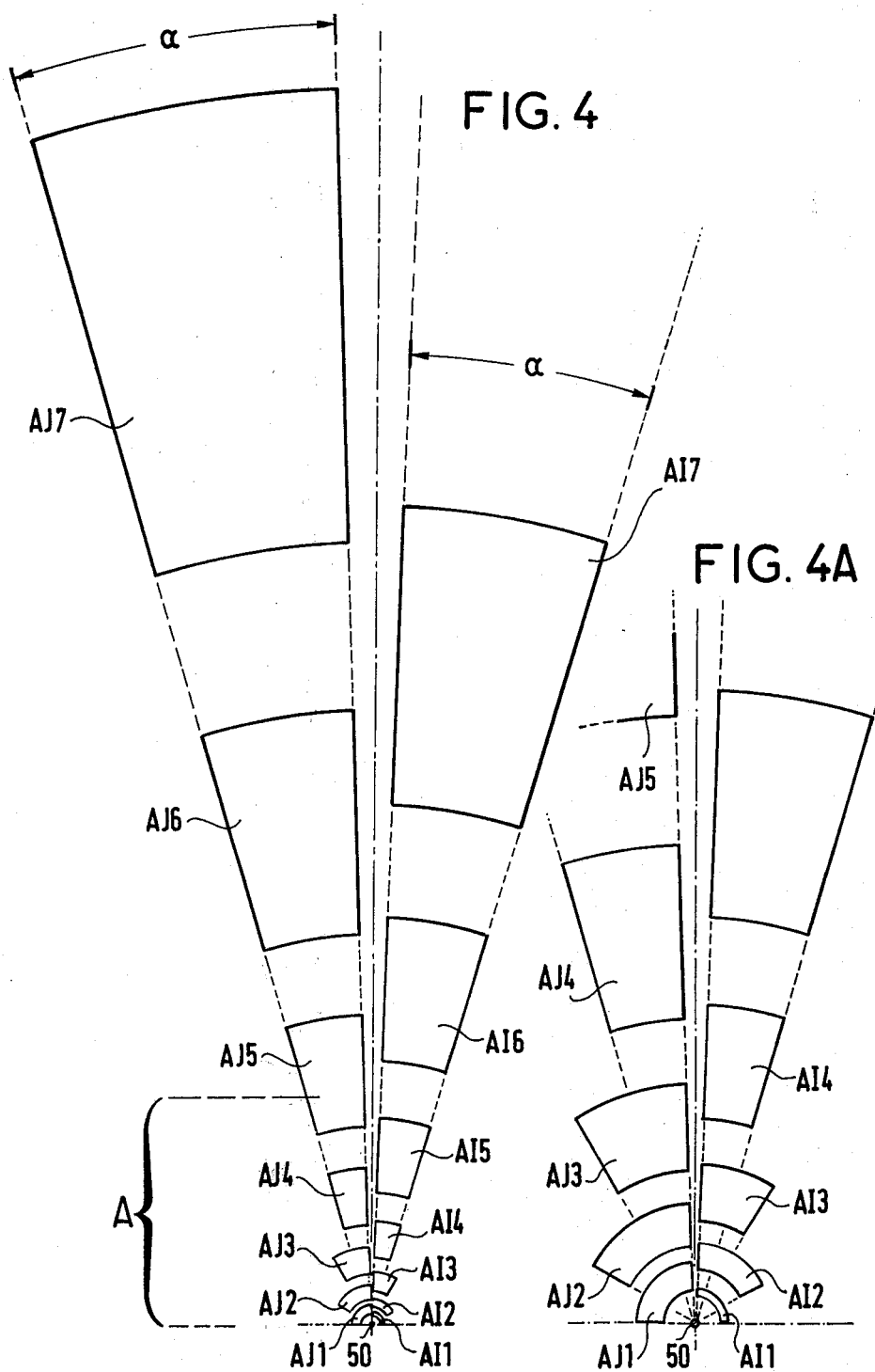

DEVICE FOR DETERMINING THE GRANULOMETRIC COMPOSITION OF A MIXTURE OF PARTICLES BY DIFFRACTION OF LIGHT

The present invention relates to a device for determining the granulometric composition of a mixture of particles by diffraction of light.

BACKGROUND

The device makes it possible to determine, in a mixture of particles or grains of various sizes, the percentage of particles whose sizes are contained between predetermined succesive ranges. The mixture is preferably in powder form and it is then transformed into a suspension of particles in a gaseous, or, more often, liquid fluid.

The suspension must be sufficiently diluted and formed as a sufficiently thin layer to enable light to pass through it and be partially diffracted by the particles.

However, the mixture can assume other forms, e.g. a biological preparation fixed on a transparent plate.

The device in accordance with the invention uses the known method of illuminating the mixture with a parallel beam of monochromatic light, forming a diffraction pattern, examining the pattern, which has circular symmetry about a centre to determine the distribution of the light flux as a function of radius (distance from the centre) and mathematically processing the signals supplied by the examination to deduce therefrom data concerning the granulometric composition. It is assumed here that the particles are spherical. Actually, they may have other shapes which can be observed beforehand by microscope examination. However, the person skilled in the art can then experimentally establish an at least approximate equivalence between each diameter of a spherical particle and a value of a characteristic size of a particle of known non-spherical shape.

For example, uses of this method are known through: French patent application No. 71 30 802 filed on Aug. 25, 1971; the corresponding to U.S. Pat. No. 3,807,864; the first French certificate of addition no. 77 27 308 to the above French patent application; an article by J. Cornillault entitled "Particle Size Analyzer" (Applied Optics Vol. 11, No. 2, February 1972, p. 265-268) and articles by Wertheimer et al. entitled "Light scattering measurements of particle distributions" (Applied Optics, vol. 15, p. 1616, June, 1976); and "Light scattering instrumentation for particulate measurements in processes" (SPIE, vol 129., Effective utilization of Optics in quality assurance, 1977).

These documents describe known methods of measuring not the illumination of the diffraction pattern for each value of the radius, but the total value of the light flux received on several "integration areas" which are each constituted, for example, by an opening formed in a screen and followed by a light detector which supplies a detection signal proportional to the flux. Such a disposition makes it possible for each light detector to receive a light flux which is sufficient for it to be measured easily and accurately. Above all, it allows an improvement in the quality of the final results, subject to a suitable choice of the shapes and dimensions of the integration areas. This is explained as follows: consider the light flux received on a very thin circular ring which is concentric to the pattern and has an inner or outer radius d, the flux is divided by the very small difference between the inner radius and the outer radius of the ring. The result of the division is a function of the radius d. This function will here be called f(d). The same function f(d) can be more precisely defined as the derivative of another function of d, here called F(d) which represents the flux received inside the circle of radius $\underline{d}$.

Each integration area extends between an inner circle of radius d1 (inner radius) and an outer circle of radius d2 (outer radius). For each value of the radius d lying between d1 and d2, the integration area, as seen from the centre of the diffraction pattern, has an angular extent A (angle at the centre) which may be constant but which may alternatively vary when the radius d changes. The angular extent can therefore be considered as a function A(d). The total flux Fk received in an integration area Sk is then equal, to within a constant, to the integral of the product A(d).F(d), with respect to the variable d, between the limits d1k and d2k, representing the values of d1 and d2 for the integration area. The values of d1k and d2k and possibly the law of variation of the angular extent 1, can be chosen at will so as to obtain from each integration area a detection signal which makes it possible to obtain final results which are as useful as possible, taking into account the aims to be achieved.

These aims can be diverse, but it is often required to obtain a histogram (or a continuous granulometric curve which contains the same data as a histogram), i.e. there is defined a continuous sequence of ranges of values of the diameter a of the particles from the smallest possible diameter to the greatest, e.g. in a geometrical progression and the percentage of the number of the particles whose diameters are contained in each of these successive ranges is to be found. There result two conflicting requirements. One is fineness of measurement, i.e. the number of ranges must be as great as possible, each of the ranges being as narrow as possible. The other requirement in independence of measurement, i.e. the percentage measured for a range must be altered as little as possible by the presence of particles whose diameters are included in the other ranges. In accordance with known dispositions, unfortunately, these two requirements cannot be achieved simultaneously, since if an increased number of narrower ranges is chosen, the percentage measured for a range will be more greatly affected by the presence of particles which correspond to several neighbouring ranges. This can be explained considering the distribution of light sent to the diffraction pattern by particles of a given diameter $\underline{a}$, the greater part of said light being distributed from the centre of the spot up to a distance d from the centre. The smaller the diameter a, the greater the distance $\underline{d}$. Therefore, to estimate the percentage of particles in a range with a diameter of about a in a mixture, it is necessary to measure the light flux in a zone of the diffraction pattern (integration area) which is sufficiently far from the centre so as not be hindered by light diffraction by the particles whose diameters come within the higher ranges and said zone must be sufficiently near to gather a significant fraction of light diffracted by the particles sought. However, light diffracted by the particles of greater diameter and especially light diffracted by particles of smaller diameter does cause slight disturbance but does not make it impossible to estimate the percentage of the particles in the range of diameters considered, since the influence of the other particles can also be taken into account when the received signals are mathematically processed, but it results in inaccurate estimation and the greater the proportion of hindering light, i.e. light diffracted in the zone in question by these other particles, the greater the inaccuracy. It is well known in metrology that such inaccuracy is observed each time an estimation is made by subtraction of two measurements which are themselves erroneous and cannot be corrected and that this inaccuracy is increased when these two measurements are close to each other.

Referring again to measurement of granulometry by diffraction of monochromatic light, there are three possibilities for keeping accuracy within acceptable limits, i.e. for keeping the estimation of the percentage of particles in one range of diameters sufficiently independent from the percentages of the other particles. A first possibility consists of choosing sufficiently large values for both the relative width of the diameter ranges (i.e. in practice the ratio between the largest and the smallest diameters in the range) and the radial extent of the areas of integration (i.e. the ratio between the greatest and smallest radius of the area). This makes it possible simultaneously to collect a large fraction of the light diffracted by the particles in the diameter range in question and to collect only a relatively smaller fraction of the light diffracted by the other particles. However, this possibility is limited by the fact that the width of the ranges becomes excessive when using the results. In practice, it is possible to continue in this way up to a relative width equivalent to 2; then the user requires a width whose value is at least that of the square root of 2, i.e. about 1.4.

A second possibility, which can be used in equipment found in trade, consists in disregarding the finest particles which cause the greatest hindrance. In practice, this is equivalent to either studying mixtures which do not include particles with a diameter of less than about one micrometer or, if the mixture includes such particles, not measuring their concentration and, what is worse, neglecting their influence, i.e. finally accepting erroneous estimations for the concentrations of particles of diameters greater than one micrometer.

A third possibility takes into consideration the fact that the hindrance due to the finest particles is connected not directly to the diameters thereof, but to the ratio between their diameters and the wavelength of the light used. This possibility consists in using light with a shortened wavelength. In practice, helium-neon laser light is used at present, its wavelength being 0.63 micrometers. This would lead to using a clearly shorter wavelength, e.g. twice as short. This would be both complex and expensive.

The present invention aims to produce a device for determining the granulometric composition of a mixture of particles by light-diffraction to make it possible in particular to obtain simply and accurately a granulometric histogram with sufficiently narrow ranges, even when the mixture studied includes particles of diameters close to the wavelength of the light used.

THE INVENTION

The invention provides a device for determining the granulometric composition of a mixture of particles by light-diffraction, said device including:

a source of monochromatic light which emits a parallel beam;

means for making the mixture pass through the beam;

an optical system for forming the diffraction pattern in the focal plane of the beam by the mixture, the pattern being circularly symmetrical about a centre constituted by the image of the parallel beam;

a system for scanning the diffraction pattern, said system including a set of light detectors each of which receives the light flux which passes through a light-integration area, each area being constituted by a predetermined portion of the diffraction pattern and having substantially the form of a segment of a circular ring which is concentric with the pattern, the ring being defined by its inner and outer radii, each detector supplying a detection signal which is representative of the light flux which it receives; and a circuit for processing the data constituted by the detection signals;

characterized in that said scanning system includes at least two successions of at least three integration areas of increasing inner and outer radii;

the inner radius of each integration area of each succession being greater than the outside radius of the preceding integration area so as to allow unoccupied ranges in the continuous sequence of the values of the radii, the ranges being located between two consecutive integration areas in the continuous sequence and being narrower than the areas;

the inner and outer radii of the areas of any one of these successions being shifted with respect to those of the areas of each other succession so that in said continuous sequence the areas of these other successions occupy the unoccupied ranges of any succession in question, extending beyond these ranges on either side.

Preferably, the inner radii of the integration areas in any single succession constitute substantially a geometrical progression with a common ratio of $r$;

the outside radius of each integration area being substantially equal to its inner radius multiplied by an integration extent factor $e$, a factor which is firstly smaller than the common ratio $r$ so as to leave said unoccupied ranges between the successive integration areas, in each succession, the factor also being greater than the square root of the common ratio $r$ so as to be less than the ratio between the inner radius of an integration area and the upper radius of the preceding integration area;

the values of the common ratio $r$ and of the extent factor $e$ being the same for both successions; and the inner radii of the areas of a succession being equal to the inner radii of the areas of the other succession multiplied by a shift factor $g$ smaller than the common ratio $r$.

THE DRAWINGS

A description of how the invention can be implemented will be given hereinafter by way of a non-limiting example and with reference to the schematic figures of the drawings. It must be understood that the components described and illustrated can be replaced by others components which fulfill the same technical functions. When a component is illustrated in several figures, it always bears the same reference symbol;

FIG. 4 is a front view of the integration areas formed on the front surface of a silicon plate which constitutes a part of the scanning system: and FIG. 4a is a view of an enlarged scale of a part A of FIG. 4.

DESCRIPTION

Figure 1:
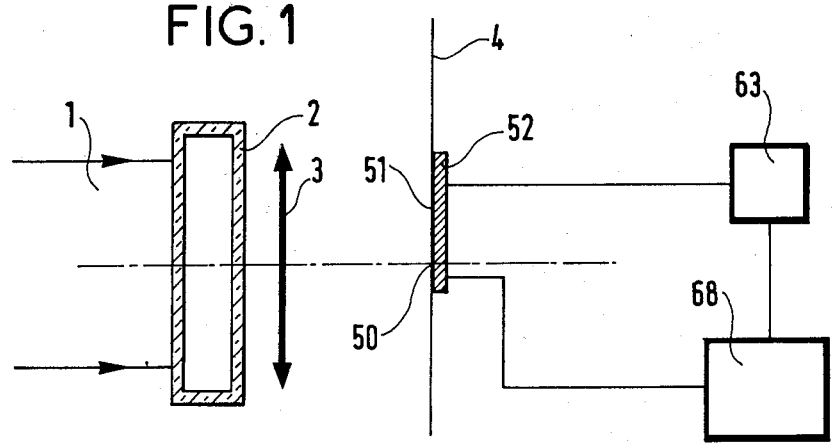
FIG. 1 is a general block diagram of one embodiment of the device in accordance with the invention.
Figure 2:
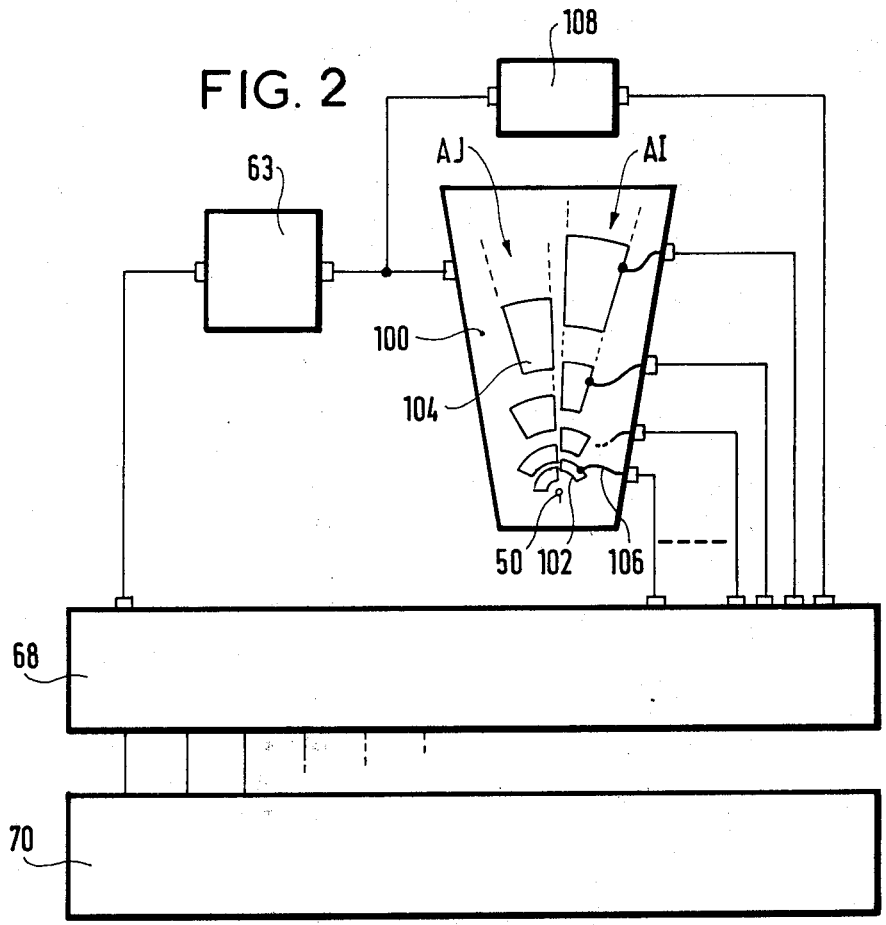
FIG. 2 is a front view of the scanning system of the device illustrated in FIG. 1.

In FIG. 1, a monochromatic light beam 1 emerges from a source such as a helium-neon type laser generator and illuminates a sample of particles in suspension in a liquid or in a gas. The sample is disposed in a transparent receptacle 2 which is advantageously in communication with a device, not shown, which causes the particles to flow continuously. A converging optical system such as a lens 3 forms in its focal plane an image of the diffraction patterns generated by an illuminated sample. The image is substantially symmetrical about a centre constituted by the image of the source, i.e. in general by the focus 50 of the lens 3.

The front surface 51 of a scanning system 52 is disposed in the focal plane 52 and includes:

a monocrystalline silicon plate 100;

photodiodes which constitute said detectors and are formed in the plate by local inversions of silicon conductivity type on a front surface of the plate, said front surface receiving light from the diffraction patterns the surfaces of the photodiodes constituting said integration areas AI, AJ;

electrodes for electric connection of the photodiodes; and electronic circuits for amplifying the detection signals supplied by these photodiodes.

There are two successions of integration areas—a succession AI and a succession AJ—but there could be a greater number thereof, e.g. three or four, to increase further the accuracy of the device. The plate 100 and these successions are disposed on a main, non-peripheral, portion of the diffraction pattern;

the scanning system further including a detector outside the silicon plate for scanning a peripheral portion of the diffraction pattern.

The detector is connected to amplifier circuit 63 and 68 and is intended to measure a light flux diffracted or diffused mainly by the finest particles of the mixture examined (i.e. those measuring less than a micrometer). The fine particles whose magnitude is about the same as that of the wavelength or even less no longer diffract light in accordance with the preceding laws, but diffuse light in a practically uniform manner up to relatively wide angles of about 50 or 60 degrees and at wider angles, they produce diffusion patterns with maxima and minima of light.

Since the variations in the flux diffused as a function of the angle are very small, it is possible to measure these particles by placing a detector constituted by a single cell in a zone sufficiently far from the axis for the illumination supplied by the larger particles not to be the largest. Therefore, the laws set forth elsewhere for the integration areas do not apply here. The theoretical fluxes received by the cell and coming from each class are calculated in the same way as the others and are introduced in the system of linear equations. More exactly, said successions of integration areas extend from the centre of the diffraction pattern up to a distance lying between 0.15 and 0.3 times the focal distance of said optical system, said detector being disposed at a greater distance, equal, for example, to 0.5 times the focal distance.

The detection signals supplied after amplification in the circuit 68 are processed in a data and display processing circuit 70. The amplification factors are adjusted so as to compensate for the differences between the angular widths of the various areas of integration and in the case of detector 108, to obtain as correct a result as possible by comparison against a standard. In a first step, the detection signal supplied by the detector will not be taken into account in the present description. There are then n integration areas in each succession and they each have the shape of an angular sector with a circular ring centred at 50. Because of the adjustment of the amplification factor, the detection signals which they supply represent the light flux received around the whole periphery of the circular ring.

The circuit 70 can include, for example:

an electronic memory for recording the n values of the detection signals, each signal being proportional to the light flux Fk or Gk which illuminates the ring which corresponds to an integration area AIk or AJk whose inner and outer radii respectively have the values d1k and d2k, k varying between 1 and n, the radii d1k forming a geometrical progression with a common ratio of r=2, for example, as is the case for the radii d2k; and a matrix inversion circuit such as a microprocessor connected to said electronic memory and capable of using the data stored in said memory and a sequence of values of diameters of particles $a_i$, said values forming a geometric progression with the same common ratio r and being chosen from among with the same common ratio r and being chosen from among possible values of diameters of particles of the mixture, i being an index which assumes the values 1 to n, the values $N_i$ being solutions of the system of equations:

$$F_k = \text{const} \sum_{i=1}^{i=n} N_i \frac{a_i^2}{2\sigma^2} \int_{a=0}^{a=\infty} \exp.-\left[\frac{[\log a - \log a_i]^2}{2\sigma^2}\right] \times \left[\left[J_0^2\left[\frac{ad_{1k}}{z}\right] + J_1^2\left[\frac{ad_{1k}}{z}\right]\right] - \left[J_0^2\left[\frac{ad_{2k}}{z}\right] - J_1^2\left[\frac{ad_{2k}}{z}\right]\right]\right] d(\log a) \quad (1)$$

$J_0$ and $J_1$ being the Bessel functions of order 0 and 1, $N_i$ being a value representative of the percentage of particles of diameter close to $a_i$ contained in the mixture being studied, $\sigma$ being equal to $(\log r)^2/2\sqrt{2} \log 2$, r being the common ratio of the geometrical progression of the values $a_i$, and z being equal to $\lambda f/\pi$.

The system of equations is equivalent to decomposing the granulometric spectrum into a number of components which intersect one another at half their height, each component having a Gaussian profile. This hypothesis is very satisfactory for powders obtained by crushing, but is unsuitable in many cases and in particular in the case of sifted powders. Indeed, it is then no longer possible to consider that the various classes extend to infinity, since there is a clear cut for the diameter which corresponds to the sieve.

A better hypothesis, which also gives good results for non-sifted powders is that of a decomposition into granulometric ranges with a constant volume distribution inside each range.

The system of equations is then as follows:

$$F_k = \text{const} \sum_{i=1}^{i=n} \frac{P_i}{a_{imax} - a_{imin}} \int_{a_i=a_{imin}}^{a_i=a_{imax}} \frac{J_o^2\left(\frac{a_i d_{1k}}{z}\right) + J_1^2\left(\frac{a_i d_{1k}}{z}\right) - J_o^2\left(\frac{a_i d_{2k}}{z}\right) - J_1^2\left(\frac{a_i d_{2k}}{z}\right)}{a_i} da_i \quad (2)$$

$a_i$, $d_{1k}$, $d_{2k}$ and Z having the same meaning as previously, $P_i$ being the weight of the particles in class i delimited by the diameters $a_{imax}$ and $a_{imin}$.

When two shifted series are used, said series supplying the fluxes $F_k$ and $G_k$, use can be made of the indications supplied by one of the series to modify the initial calculation hypothesis of the other.

To do this, the values of $P_{j-1}$ and $P_j$ are calculated, these values lying on either side of the value $P_i$, which is the weight of the particles in class i, and the law of distribution inside this class is related to the measurements $P_{j-1}$ and $P_j$. On considering the function $$S_{j-1,j} = \frac{P_j - P_{j-1}}{P_j + P_{j-1}}, \quad (3)$$

which indicates the relative differences between the populations of classes j-1 and j, it can be assumed that the population of class i is distributed proportionally to this value instead of evenly.

The preceding equation then becomes:

$$F_k = \text{const} \sum_{i=1}^{i=n} \frac{P_i}{a_{imax} - a_{imin}} \int_{a_i=a_{imin}}^{a_i=a_{imax}} \frac{J_o^2\left(\frac{a_i d_1}{z}\right) + J_1^2\left(\frac{a_i d_{1k}}{z}\right) - J_o^2\left(\frac{a_i d_{2k}}{z}\right) - J_1^2\left(\frac{a_i d_{2k}}{z}\right)}{a_i} \times \quad (4)$$

$$K \times S_{j-1,j} \times (a_i - a_{imin}) da_i$$

Then a second calculation must be made to obtain a final distribution.

To avoid a fairly long calculation at each measurement, the influence of the preceding correction can very well be calculated. For several values of S of each group of two classes, the corresponding inverted matrices can be calculated and the correcting coefficients can be defined in the form of the gradient of a linear regression.

The matrix inversion circuit carries out the same operation based on the fluxes Gk and on diameter values aj to obtain values Nj. In each case, the sequence of the values ai or aj is such that this sequence correspondence between this sequence and that of the radii of the integration areas. More exactly, the values of these radii are chosen so that the flux received on each of the integration areas is as representative as possible of the percentage of the particles situated in a corresponding range centreed on one of the values ai or aj.

In practice, the average value of the radius of an integration area i.e. the geometrical average of the inner radius and of the outer radius is chosen equal to .325f/ai.

Therefore, two histograms are obtained which correspond to two successions shifted by consecutive ranges, the mutual shift factor of these two successions being equal to that of the two successions of integration areas, i.e. the square root of two. The average of these two histograms can then be found so as to obtain a new histogram which is finer, i.e. with ranges in each of which the ratio of the end diameters is equal to the square root of two.

Figure 3:
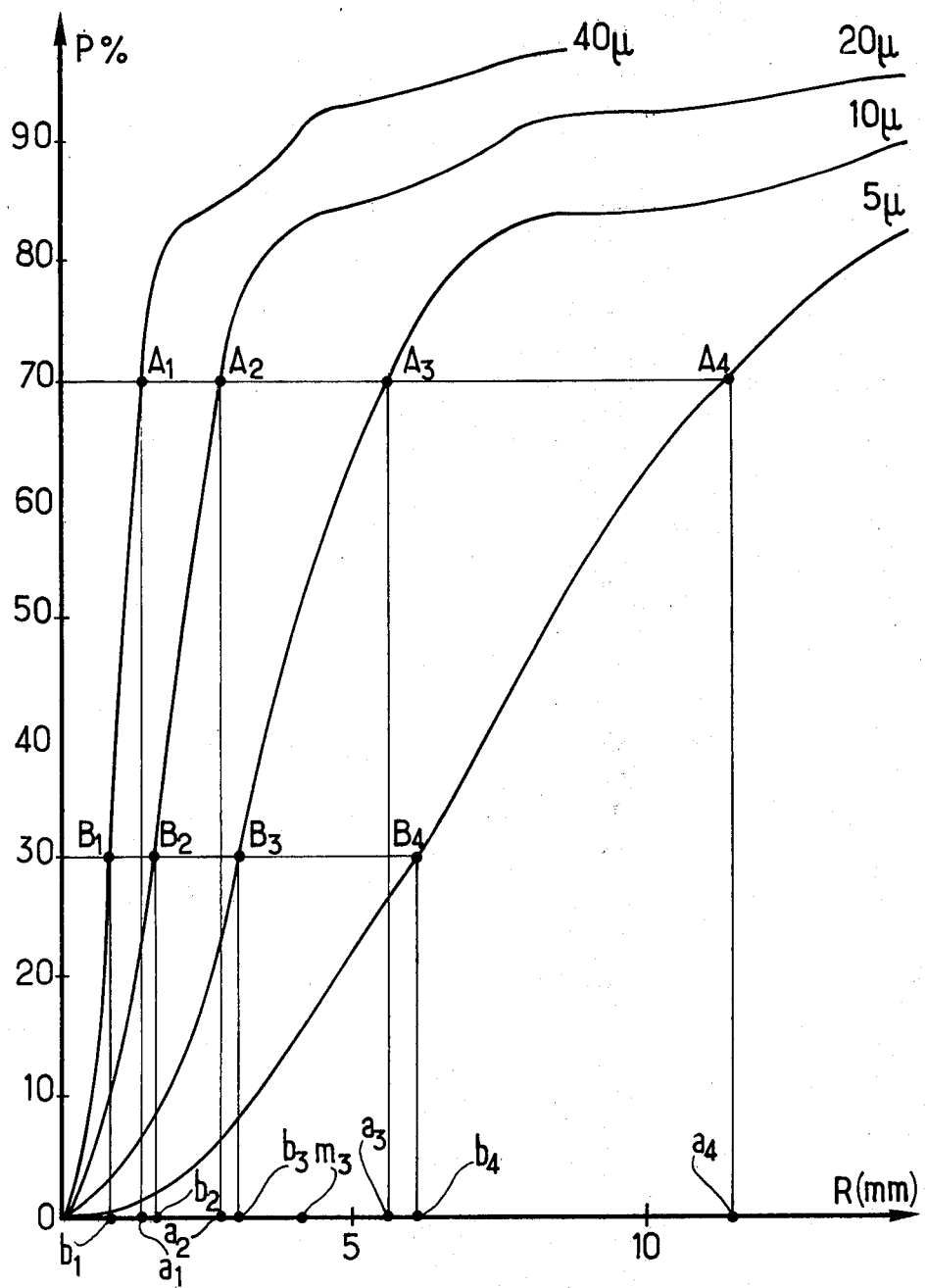
FIG. 3 is a network of curves which represent, for a sample of monodispersed particles, the distribution of the light energy in the image of the diffraction spot associated with the sample, for different values of the diameter of the particles.

One way of choosing the integration areas will now be explained more precisely with reference to FIGS. 3 and 4.

A network of curves is traced in a system of axes of rectangular co-ordinates OR, OP, said curves showing the variation of the percentage P of the light energy diffracted in a circle as a function of the value R of the radius of the circle expressed in millimeters, the parameter taken being the diameter of the particles. Each curve corresponds to a set of monodispersed particles, i.e. to a set of particles composed of particles all of the same diameter. FIG. 3 illustrates, for example, four curves P=f(R) which correspond respectively to the diameters 40, 20, 10 and 5 microns distributed in a geometrical progression with a common ratio of 2. These curves, plotted for a focal distance of 120 mm from the optical system which forms the diffraction image have been determined on the basis of theoretical considerations. On each of these curves, a portion of maximum gradient is defined, said portion lying between two straight lines parallel to the R axis, whose respective ordinates are, for example, equal to 70% and to 30%, as illustrated in FIG. 3. The straight line whose ordinate is 70% intersects the curves respectively at the points $A_1$, $A_2$, $A_3$ and $A_4$ and the straight line whose ordinate is 30% at the points $B_1$, $B_2$, $B_3$ and $B_4$. These steep portions $A_1,B_1,A_2,B_2,A_3,B_3$ and $A_4,B_4$ are projected onto the axis R so as to obtain respective segments $a_1b_1, a_2b_2, a_3b_3$ and $a_4b_4$.

It will be observed that in the plane of the diffraction pattern, the segment $a_1b_1$, for example, defines a zone limited by the circles of radii $Oa_1$ and $Ob_1$, where the light power diffused comes mainly from particles having diameters of 40 microns or close to 40 microns. The segment $a_2b_2$ relates in the same way to the light diffused by particles with a diameter of 20 microns, and so on. That is why a priori it is advantageous to place the integration areas in the circular rings which correspond to these portions of maximum gradient, it being understood, however, that the above-mentioned 30% and 70% to delimit these portions are not the best for determining the radial extent of the integration areas, the preferred values of the radial extent being indicated hereinafter.

It should also be observed that the various curves are deduced from one another simply by changing the scale of their X axes; that is why firstly the length of the segments such as $a_3b_3$ is proportional to the X axis of their mid points such as $m_3$ and secondly the maximum gradient portions of the various curves are all located between two straight lines which are parallel to the X axes.

It is also apparent that if diameter values distributed in a geometrical progression with a common ratio r smaller than two, e.g. 1.4 had been chosen to plot the network of curves and if integration areas distributed in a corresponding geometrical progression with the same common ratio smaller than two, the result would have been that the hindering portion of energy received on an integration area would have been greater, the hindering energy being that which is sent by the particles whose diameter does not coincide with the diameter range to which the integration area is assigned.

Also, research work carried out within the scope of the invention shows that to increase the contrast, i.e. to reduce the proportion of hindering energy with respect to the useful energy received on each integration area, it is preferable for the ranges between radii occupied by the integration areas not to form a continuous sequence, in each successsion i.e. in each succession it is preferable to leave empty radius ranges between two successive integration areas.

If, as known, there had been only one succession of integration areas, these unoccupied ranges would evidently cause part of the data contained in the diffraction pattern to be lost. The use, in accordance with the invention, of a second succession of integration areas suitably shifted with respect to the first integration area allows such loss of information to be avoided without reducing the contrast.

With reference to FIG. 4, each succession of integration areas AI or AJ includes 7 areas in the form of angular sectors of circular rings centred at 50. The inner and outer raddi form geometrical progressions with a common ratio $r = 2$, the shift factor g being equal to the square root of two. The exent factor e is 1.57.

Although it has the advantage of simplicity, the angular sector shape of the circular ring is evidently not necessary, but for the mathematical formulas used to be valid, the angular extent A must remain constant in each area of integration. Other formulas must be used if the angular extent varies within the integration areas. However, the angular extent can vary from one integration area to the next without any modification of the mathematical formulae.

In the embodiment described here, the first three integration areas of each succession have been chosen with an increased angular extent so that the corresponding detectors receive a sufficient light flux taking into account their small size and possibly the low proportion of large-diameter particles in the mixtures studied. It is easy to compensate these differences in angular extent when the detection signals are amplified. The angular extent can be chosen, in fact, up to 180° in the case of two successions.

More generally, the following choices of characteristics seemed preferable:

the common ratio r lies between 1.5 and 3, the extent factor e lying between 0.7 r and 0.9 r.

It seems that it would be even more advantageous for the common ratio 2 to lie between 1.8 and 2.4.

the number of said successions is two, the shift factor g lying between 1.3 and 1.6.

whatever the number of successions may be, the shift factor g between a pair of said successions is substantially equal to a root of the common ratio r, the order of the root being the number of successions.

Of course, it would be possible to electronically produce successions of integration areas equivalent to those described hereinabove, but giving them a different physical appearance. To do this, it is possible, for example, to use a single succesion of photodiodes each of which allows the flux received on a very thin circular ring which is concentric with the diffraction spot, the large number of photodiodes allowing the whole radial extent of the spot to be covered.

Each of the previously defined detection signals would then be formed by adding elementary signals supplied by a number of consecutive and suitably amplified photodiode, the choice of the number and the positions of the photodiodes then defining an integration area which satisfies the above-defined rules. The elementary signals of some of these photodiodes are used to form two different detection signals. Adjusting the amplification factors it is possible, in principle, thus to form a detector such as previously described, i.e. a detector capable of supplying a detection signal which is representative of the light flux received on an integration area such as previously defined. However, such a disposition does not seem desirable for the moment, since firstly it increases the complexity of the scanning system and secondly it brings about errors which are detrimental to the final precision of the device.

I claim:

1. A device for determining the granulometric composition of a mixture of particles by light-diffraction, said device including:

a source of monochromatic light which emits a parallel beam (1);

means (2) for making the mixture pass through the beam;

an optical system for forming the diffraction pattern in the focal plane 4 of the beam by the mixture, the pattern being circularly symmetrical about a centre (5) constituted by the image of the parallel beam;

a system for scanning the diffraction pattern, said system including a set of light detectors (102, 104) each of which receives the light flux which passes through a light-integration area (AI, AJ), each area being constituted by a predetermined portion of the diffraction pattern and having substantially the form of a segment of a circular ring which is concentric with the pattern, the ring being defined by its inner and outer radii, each detector supplying a detection signal which is representative of the light flux which it receives; and a circuit (70) for processing the data constituted by the detection signals; characterized in that said scanning system includes at least two successions (AI,AJ) of increasing inner and outer radii;

the inner radius of each integration area of each succession (AI) being greater than the outside radius of the preceding integration area so as to allow unoccupied ranges in the continuous sequence of the values of the radii, the ranges being located between two consecutive integration areas in the continuous sequence and being narrower than the areas;

the inner and outer radii of the areas of any one of these successsions being shifted with respect to those of the areas of each other successions so that in said continuous sequence the areas of these other succesions occupy the unoccupied ranges of any succession in question, extending beyond these ranges on either side.

2. A device according to claim 1, characterized in that the inner radii of the integration areas in any single succession (AI) constitute substantially a geometrical progresssion with a common ratio of r;

the outside radius of each integration area being substantially equal to its inner radius multiplied by an integration extent factor e, a factor which is firstly smaller than the common ratio r so as to leave said unoccupied ranges between the successive integration areas, in each succession, the factor also being greater than the square root of the common ratio r so as to be less than the ratio between the inner radius of an integration area and the upper radius of the preceding integration area;

the values of the common ratio r and of the extent factor e being the same for both successions (AI,AJ); and the inner radii of the areas of a succession (AJ) being equal to the inner radii of the areas of the other succession (AI) multiplied by a shift factor g smaller than the common ratio r.

3. A device according to claim 2, characterized in that the common ratio r lies between 1.5 and 3, the extent factor e lying between 0.7 r and 0.9 r.

4. A device according to claim 3, characterized in that the common ratio r lies between 1.8 and 2.4.

5. A device according to claim 2, characterized in that the number of said successions (AI, AJ) is two, the shift factor g lying between 1.3 and 1.6.

6. A device according to claim 2, characterized in that the shift factor g between two said successions (AI,AJ) is substantially equal to a square root of the common ratio r, the order of the square root being the number of the successions.

7. A device according to claim 1, characterized in that said segments of circular rings are angular sectors of circular rings.

8. A device according to claim 1, in which said scanning system (52) includes:

a monocrystalline silicon plate 100;

photodiodes which constitute said detectors (102,104) and which are formed in the plate by localized inversions of the type of conductivity of the silicon on a front surface of the plate which receives light from the diffraction spot, the surfaces of the photodiodes constituting said integration areas AI;

electrodes (106) for electrically connecting the photodiodes; and electronic amplification circuits (63,68) for the detection signals supplied by these photodiodes;

characterized in that said successions of integration areas (AI, AJ) formed by said photodiodes on said silicon plate (100) are disposed on a main non-pheripheral portion of the diffraction pattern;

the scanning system further including a detector (108) outside the silicon plate to scan a peripheral portion of the diffraction pattern.

9. A device according to claim 8, characterized in that said successions of integration areas (AI) extend from the centre (50) of the diffraction pattern up to a distance which lies between 0.15 and 0.3 times the focal distance of said optical system (3), said outer detector (108) being disposed at a greater distance.

* * * * *